US011026609B2

(12) United States Patent
Biederman et al.

(10) Patent No.: US 11,026,609 B2
(45) Date of Patent: Jun. 8, 2021

(54) WAKE-UP BATTERIES FOR INVASIVE BIOSENSORS

(71) Applicant: Verily Life Sciences LLC, Mountain View, CA (US)

(72) Inventors: William Biederman, Oakland, CA (US); Zenghe Liu, Alameda, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 496 days.

(21) Appl. No.: 15/232,296

(22) Filed: Aug. 9, 2016

(65) Prior Publication Data

US 2018/0042538 A1 Feb. 15, 2018

(51) Int. Cl.
*A61B 5/1486* (2006.01)
*H01M 4/02* (2006.01)
(Continued)

(52) U.S. Cl.
CPC ........ *A61B 5/14865* (2013.01); *A61B 5/0024* (2013.01); *A61B 5/1451* (2013.01);
(Continued)

(58) Field of Classification Search
CPC ............ A61B 5/14532; A61B 5/14865; A61B 5/0002; A61B 5/14503; A61B 2562/02;
(Continued)

(56) References Cited

U.S. PATENT DOCUMENTS 3,837,339 A * 9/1974 Aisenberg ............ A61B 5/0002
604/504
6,217,744 B1 4/2001 Crosby et al.
(Continued)

FOREIGN PATENT DOCUMENTS

TW 201339567 10/2013
WO 2015084269 6/2015

OTHER PUBLICATIONS

Definition of a fuel cell from https://www.energy.gov/eere/fuelcells/fuel-cells, obtained Aug. 2020 (Year: 2020).*
(Continued)

*Primary Examiner* — Christian Jang
*Assistant Examiner* — Karen E Toth
(74) *Attorney, Agent, or Firm* — Kilpatrick Townsend & Stockton LLP (57) ABSTRACT

Example biosensor devices having wake-up batteries and associated methods are disclosed. One example device includes a biosensor that has a first electrode for insertion into a subcutaneous layer beneath a patient's skin, and a second electrode coupled to the first electrode for insertion into the subcutaneous layer, and a first battery to apply a voltage across the first and second electrodes, the first battery at least partially electrically decoupled from the electrodes. The device also includes a second battery having an anode material coupled to the first electrode for insertion into the subcutaneous layer, and a portion of the second electrode. The second battery is activatable upon immersion in an electrolytic fluid. The device also includes a wake-up circuit to receive a signal from the second battery and, in response, to electrically couple the first battery to the first and second electrodes to activate the biosensor.

19 Claims, 7 Drawing Sheets

(51) Int. Cl.
*H01M 8/083* (2016.01)
*A61B 90/98* (2016.01)
*A61B 5/00* (2006.01)
*A61B 5/145* (2006.01)
*H01M 6/34* (2006.01)

(52) U.S. Cl.
CPC .......... *A61B 5/14532* (2013.01); *A61B 90/98* (2016.02); *H01M 4/02* (2013.01); *H01M 6/34* (2013.01); *H01M 8/083* (2013.01); *A61B 2560/0209* (2013.01); *A61B 2560/0214* (2013.01)

(58) Field of Classification Search
CPC ........... A61B 5/1486; A61M 2230/201; C12Q 1/006; H01M 8/083; H01M 4/02; C23F 13/02
See application file for complete search history.

(56) References Cited

U.S. PATENT DOCUMENTS

| | | | |
|---|---|---|---|
| 2004/0066262 A1 | 4/2004 | Wenner et al. | |
| 2004/0263264 A1* | 12/2004 | Yin | H03B 5/06 331/57 |
| 2008/0284599 A1 | 11/2008 | Zdeblick et al. | |
| 2010/0213082 A1* | 8/2010 | Feldman | A61B 5/1486 205/777.5 |
| 2010/0324392 A1* | 12/2010 | Yee | A61B 5/14532 600/345 |
| 2013/0090534 A1* | 4/2013 | Burns | A61B 3/16 600/301 |
| 2015/0150480 A1* | 6/2015 | Zdeblick | A61B 5/0031 600/302 |

OTHER PUBLICATIONS

International Application No. PCT/US2017/042052, "International Search Report and Written Opinion", dated Oct. 16, 2017, 15 pages.
International Application No. PCT/US2017/042052, "International Preliminary Report on Patentability", dated Feb. 21, 2019, 10 pages.
European Application No. 17745228.1, Notice of Decision to Grant, dated Nov. 26, 2020, 1 page.
Taiwan Application No. 106126504, Office Action, dated Mar. 8, 2021, 14 pages.

* cited by examiner

WAKE-UP BATTERIES FOR INVASIVE BIOSENSORS

FIELD

The present disclosure generally relates to invasive biosensors and more specifically to wake-up batteries for invasive biosensors.

BACKGROUND

Invasive biosensors, such as implantable glucose sensors, may use a battery to power sensor components or other circuits or electronics to obtain information from the sensor components and to transmit the information to another device. However, while the biosensor sits idle, e.g., in a package on a shelf, its battery may slowly discharge over time before the sensor is used, thereby reducing the useful life of the sensor.

SUMMARY

Various examples are described for wake-up batteries for invasive biosensors. For example, one disclosed device includes a biosensor comprising a first electrode having a distal end for insertion into a subcutaneous layer beneath a patient's skin, a second electrode coupled to the first electrode, a portion of the second electrode for insertion into the subcutaneous layer, and a first battery to apply a voltage across the first and second electrodes, the first battery at least partially electrically decoupled from the electrodes; a second battery comprising an anode material coupled to a portion of the distal end of the first electrode, the anode material for insertion into the subcutaneous layer, and a portion of the second electrode, the second battery activatable upon immersion in an electrolytic fluid; and a wake-up circuit coupled to the second battery to receive a signal from the second battery and, in response, to electrically couple the first battery to the first and second electrodes.

One disclosed method includes inserting an insertable portion of a biosensor and a second battery into a patient's skin and into the patient's interstitial fluid, the insertable portion comprising: a distal end of a first electrode and a portion of second electrode, the first electrode coupled to the second electrode, the biosensor further comprising a first battery to apply a voltage across the first and second electrodes, the first battery at least partially electrically decoupled from the electrodes, the second battery comprising an anode material coupled to a portion of the distal end of the first electrode and a portion of the second electrode; generating a signal by the second battery after the second battery is immersed in the patient's interstitial fluid; electrically coupling the first battery to the first and second electrodes by a wake-up circuit in response to receiving the signal from the second battery; and providing sensor information from the biosensor to a radio frequency ("RF") transmitter.

Another disclosed device includes a biosensor comprising: a first electrode having a distal end for insertion into a subcutaneous layer beneath a patient's skin, and a second electrode coupled to the first electrode, a portion of the second electrode for insertion into the subcutaneous layer, and a first battery comprising: an anode material coupled to a portion of the distal end of the first electrode, the anode material for insertion into the subcutaneous layer, and a portion of the second electrode, the first battery activatable upon immersion in an electrolytic fluid to apply a voltage to the first and second electrodes.

A further disclosed method includes inserting an insertable portion of a biosensor and a second battery into a patient's skin and into the patient's interstitial fluid, the insertable portion comprising: a distal end of a first electrode and a portion of second electrode, the first electrode coupled to the second electrode, the biosensor further comprising a first battery to apply a voltage across the first and second electrodes, the first battery at least partially electrically decoupled from the electrodes, the second battery comprising an anode material coupled to a portion of the distal end of the first electrode and a portion of the second electrode; generating a signal by the second battery after the second battery is immersed in the patient's interstitial fluid; electrically coupling the first battery to the first and second electrodes by a wake-up circuit in response to receiving the signal from the second battery; and providing sensor information from the biosensor to a radio frequency ("RF") transmitter.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIGS. 2A-3 show example biosensors with wake-up batteries;

DETAILED DESCRIPTION

Examples are described herein in the context of wake-up batteries for invasive biosensors. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Illustrative Example of a Wake-Up Battery for an Invasive Biosensor

Figure 1:
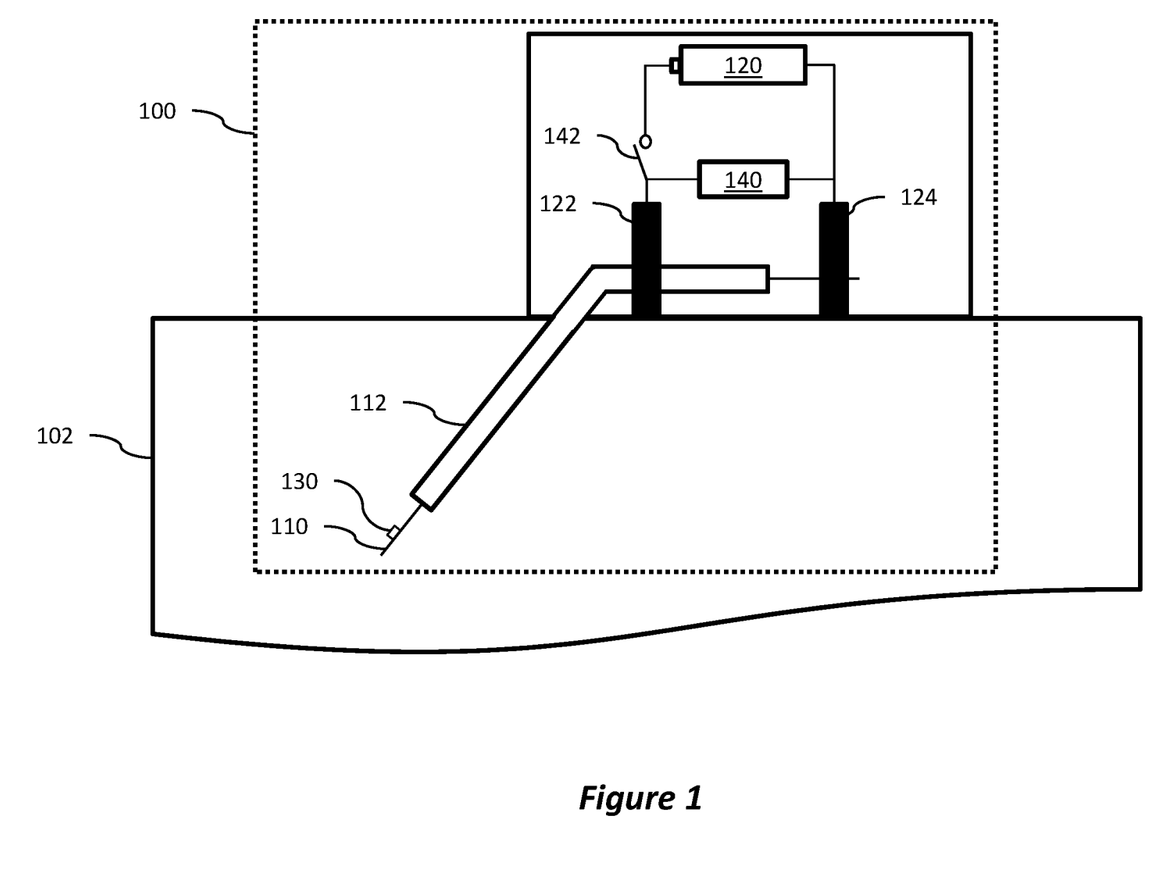
FIG. 1 shows an illustrative example glucose sensor with a wake-up battery.

One example invasive sensor shown in FIG. 1 is a glucose sensor 100. This example glucose sensor 100 has two electrodes 110, 112 that are inserted into a patient's skin 102 to expose the electrodes 110, 112 to interstitial fluid, from which glucose readings may be taken. In this example, the two electrodes 110, 112 are (1) a platinum or platinum-coated wire 110, and (2) a silver/silver-chloride (Ag/AgCl) material 112 that covers a part of the wire 110. One end of the wire 110 and a portion of the Ag/AgCl material 112 are inserted into the patient's skin 102, while the other end of the wire 110 is attached to one terminal 124 of a battery 120 and another portion of the Ag/AgCl material 112 is attached to the other terminal 122 of the battery 120.

The portion of the wire 110 that is inserted into the patient's skin 102 also has a glucose oxidase ("GOX") coating that will react to glucose present within the patient's interstitial fluid. When the wire 110 and the invasive portion of the Ag/AgCl material 112 are inserted into the patient's skin 102, the GOX reacts with glucose, which creates reaction products, such as hydrogen peroxide. When a voltage is applied to the electrodes 110, 112, an electrical current is generated based on the amount of these reaction products generated by the glucose/GOX reaction. The electrical current is then detected and the strength of the current indicates the amount of glucose that is present.

However, an invasive sensor, such as this example glucose sensor 100, may sit idle for an extended period of time, e.g., several months or more in storage, before it is used. If the glucose sensor 100 is not disabled while it is idle, the battery 120 may drain, reducing or, if the battery drains entirely, eliminating the useful life of the glucose sensor 100. To reduce or eliminate premature discharge of the battery 120, a second battery may be constructed from the glucose sensor components by affixing a small amount of an anode material 130, such as zinc, to the end of the wire 110 that is inserted into the patient's skin 102. The anode material 130 in conjunction with the Ag/AgCl material 112 and the patient's interstitial fluid creates a small battery that generates a current from the two electrodes 110, 112 of the glucose sensor 100. The current generated by this second battery is independent of any glucose/GOX reaction. The second battery, which may be referred to as a "wake-up" battery in this disclosure, therefore generates a current that can be used to enable or "wake-up" the glucose sensor 110 by activating a circuit 140 that connects the battery 120 to the electrodes via, e.g., a potentiostat (not shown), such as by closing a switch 142. It may also connect the battery 120 to other circuits within the glucose sensor 100, such as a radio frequency ("RF") transmitter (not shown) to transmit glucose sensor readings. Once the glucose sensor 100 is enabled, the main battery 120 can supply the voltage to the electrodes 110, 112 and the glucose levels in the interstitial fluid can be measured.

However, because glucose sensor readings are based on currents generated by the two electrodes, the current generated by the wake-up battery may interfere with the glucose sensor readings. Thus, the wake-up battery is created by using only a small amount of the anode material 130. For example, a suitable amount of anode material 130 may be 10 nanograms ("ng") of zinc. As a result, the wake-up battery is able to supply enough electric current to activate the electronic circuitry powered by the first battery that enables the glucose sensor 100, but then quickly dies. Once the wake-up battery is dead, the glucose sensor 100 can provide reliable glucose information.

This illustrative example is given to introduce the reader to the general subject matter discussed herein and the disclosure is not limited to this example. The following sections describe various additional non-limiting examples and examples of systems and methods for wake-up batteries for invasive biosensors.

Figures 2A, 2B, 2C:
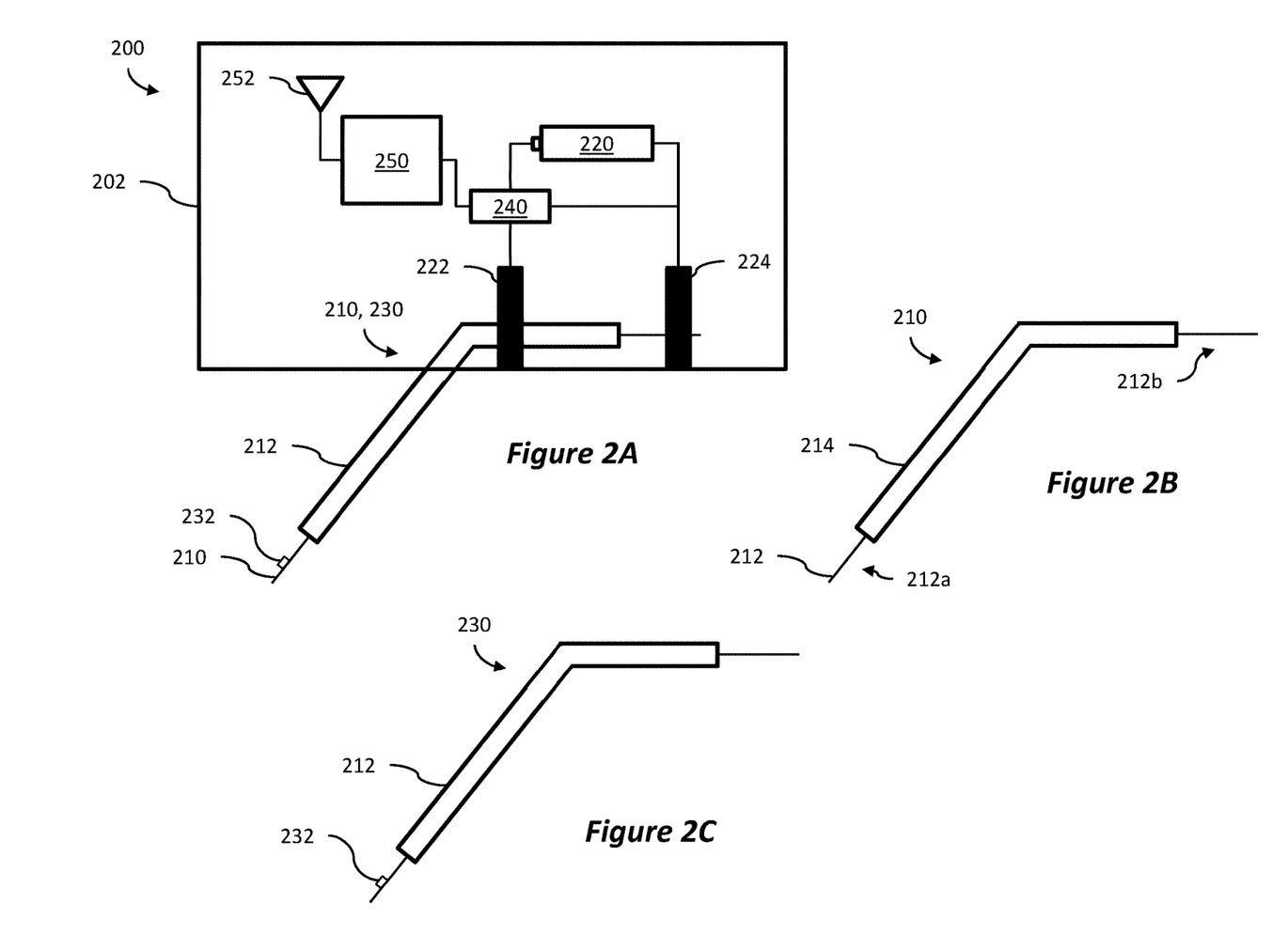

Referring now to FIGS. 2A-2B, FIG. 2A shows an example wake-up battery for a biosensor. In this example, the biosensor 200 is a glucose sensor, but in other examples the biosensor 200 may be a suitable sensor that is inserted into a patient's skin or other tissue, such as a blood oxygen sensor.

The biosensor 200 includes a sensor element 210, which is shown in isolation in FIG. 2B. The sensor element 210 includes an electrode 212 and a counter electrode 214. The counter electrode 214 is applied to the electrode 212 as a coating or sheath that partially covers the electrode 212, while leaving a portion of both the distal and proximal ends 212a-b of the electrode 212 exposed. The sensor also includes two conductive contacts 222-224 that are each connected to one of the electrode 212 or the counter electrode 214.

The biosensor 200 also includes a battery 220, a wake-up circuit 240, a transmitter 250, and an antenna 252. The negative or ground terminal of the battery 220 is connected to one of the conductive contacts 224 and is the positive terminal of the battery 220 is selectively connected to the other conductive contact 222. In this example, the conductive contacts 222-224 are conductive rubber contacts, but in other examples, other suitable conductive materials, such as conductive metals, may be used.

The wake-up circuit 240 is connected to both conductive contacts 222-224 and to the positive terminal of the battery 220. The wake-up circuit 240 can selectively connect the positive terminal of the battery 220 to the corresponding conductive contact 222. In addition, in this example, the wake-up circuit 240 can also selectively connect the positive terminal of the battery 220 to the transmitter 250. The transmitter can provide sensor data to a remote device by transmitting the data using the antenna 252. In some examples, the transmitter 250 and antenna 252 can communicate using suitable communication techniques, such as radio frequency identification ("RFID"), near-field communication ("NFC"), or BlueTooth™. For example, a remote device with an RFID or NFC reader may be brought into proximity of the antenna 252 and cause the transmitter 250 to transmit sensor information to the remote device.

The electrode 212 and counter electrode 214 are each connected to a different conductive contact 222-224, and during operation can receive a voltage applied to the conductive contacts 222-224 and supply a current to the conductive contacts 222-224 based on reactions occurring in the patient's interstitial fluid.

In this example, the electrode 212 is a platinum wire, though in some examples, the electrode 212 may be a platinum-coated wire. A platinum coating may be applied to a base wire by any suitable technique, including electroplating or physical vapor deposition, including evaporation and sputtering techniques. While a platinum material for a wire or coating for a wire may be suitable for a glucose sensor, other materials may be used according to other examples, based on the application or the desired reaction.

The counter electrode 214 in this example is a silver/silver-chloride (Ag/AgCl) coating that is applied to the electrode 212. However, any suitable coating or sheath may be deposited, sintered, overlaid, or otherwise applied to the electrode to provide a counter electrode 214. Further, while a silver/silver-chloride material may be suitable for a glucose sensor, other materials may be used according to other examples, based on the application or the desired reaction.

Figure 3:
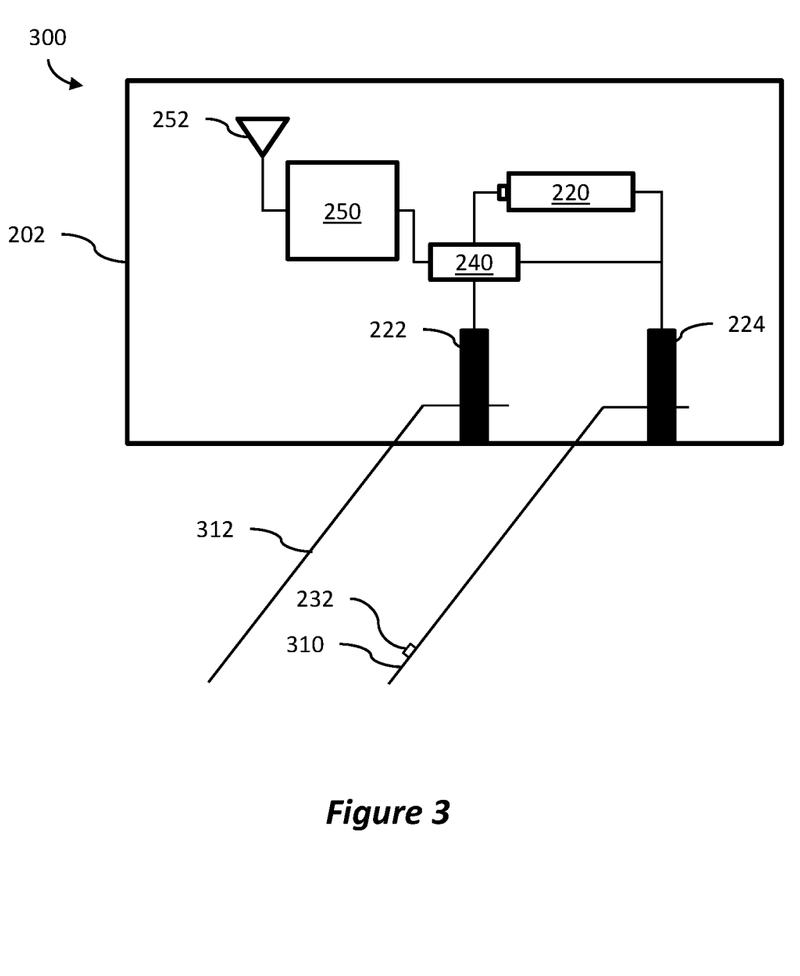

In some examples, the counter electrode 214 may be physically separate from the electrode 212. FIG. 3 shows an example sensor 300 having a counter electrode 312 physically separate from the electrode 310. In this example, the counter electrode 312 includes a second wire that can be separately inserted through a patient's skin and into the patient's interstitial fluid.

Referring again to FIG. 2A, the biosensor 200 also includes a second battery 230, shown in FIG. 2C. The second battery 230 has two components, that when immersed in an electrolytic fluid, generate a current. The first component of the second battery 230 is an anode material 232 deposited on the electrode 212. The second component of the second battery 230 is the counter electrode 214 of the sensor element 210. The anode material 232 is deposited on the end of the electrode 212 that is inserted into the patient's interstitial fluid, referred to as the "distal" end 212*a*, thus allowing the anode material 232 to be immersed in the interstitial fluid, which is an electrolytic fluid.

In this example, the anode material 232 is zinc, however, other suitable materials may be used, such as iron, aluminum, or nickel. The amount of anode material that is deposited on the electrode can depend on the amount of power needed to "wake-up" the biosensor 200. The biosensor 200 shown in FIG. 2 has approximately 10 ng of zinc as the anode material 232, which should provide approximately 100 nanoamps ("nA") or 0.6 to 0.8 volts for approximately five minutes; however, up to approximately 100 ng of zinc may be applied, which should provide approximately 100 nA or 0.6 to 0.8 volts for approximately 50 minutes. For some other anode materials, such as iron and nickel, suitable amounts of the anode material may also be between approximately 10-100 ng. For a second battery 230 constructed using aluminum, suitable amounts of aluminum may be approximately 30 percent of the amount of zinc, e.g., between approximately 3-30 ng. Such amounts of anode material 232 should generate similar amounts of current and voltage for similar amounts of time as discussed above with respect to zinc.

Selection of the amount of anode material 232 can be based on power requirements to "wake-up" other circuitry in the biosensor 200 as well as a desired amount of time during which to provide the power from the second battery 230. The sensor element 210, when active, also generates a current; however, in this example, this current is used to determine an amount of glucose present in the interstitial fluid. If the second battery 230 is generating current concurrently with the sensor element 210, the biosensor 200 may not be able provide reliable glucose level information. Thus, the amount of anode material 232 can be selected to minimize the life of the second battery 230, while still providing sufficient current to wake up the biosensor 200. As discussed above, in this example, the second battery 230 will provide current for approximately five minutes; however, other examples may require more time or power to wake up the biosensor 200.

As discussed above, the wake-up circuit 240 is connected to each of the conductive contacts 222-224. While the second battery 230 is generating a current, the wake-up circuit 240 receives the current via the conductive contacts 222-224, e.g., from the second battery 230, and, when activated by the second battery 230, it connects the battery 220 to the conductive contact 224 via a potentiostat, which is incorporated into the wake-up circuit 240, and to the RF transmitter 250. The potentiostat will then provide a voltage to the sensor element 210, which will begin sensing an amount of glucose present in the patient's interstitial fluid in this example.

Figure 4:
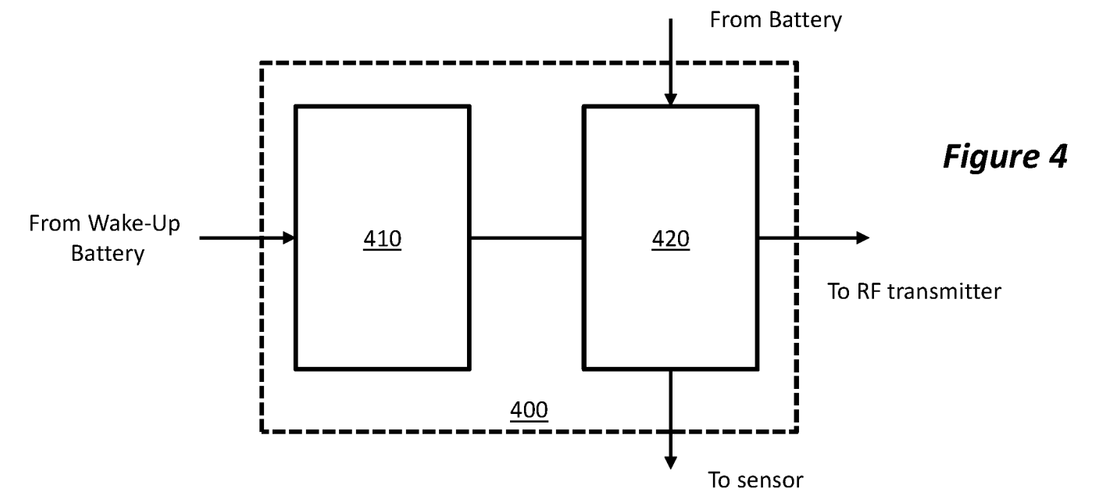
FIGS. 4-6 show example wake-up circuits suitable for use with example biosensors with wake-up batteries.

Referring now to FIG. 4, FIG. 4 shows an example wake-up circuit 400. The wake-up circuit 400 is shown as a combination of a detector 410 and an activator 420; however, this should not be read to require that the wake-up circuit requires separate detection and activation components. The detector 410 receives an input signal from the wake-up battery, e.g., wake-up battery 230. The input signal may be a current or a voltage in various examples. The detector 410 receives the input signal and determines whether the input signal indicates that the wake-up battery has been activated. If the detector 410 determines that the wake-up battery has been activated, it transmits a signal to the activator 420, which connects the battery 220 to the sensor element 210 via a potentiostat and, in some examples, activates other components or processing.

Figure 5:
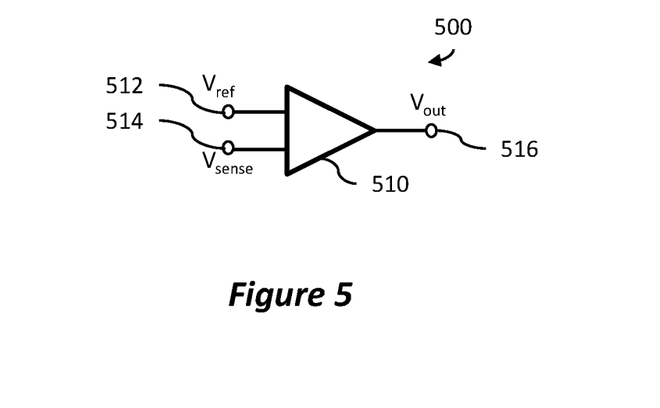

In this example, the detector 410 includes a voltage threshold detector 500, shown in FIG. 5. The voltage threshold detector 500 includes a comparator circuit 510 that accepts a reference voltage 512 from the battery 220 and a sensed voltage 514 from the second battery 230. If the sensed voltage exceeds the reference voltage, the comparator circuit 510 outputs via output terminal 516 a non-zero voltage, otherwise the comparator circuit 510 outputs zero volts. The activator 420 in this example includes a transistor. The output of the comparator circuit 510 is connected to the transistor and turns the transistor on, connecting the battery 220 to the sensing element 210 via a potentiostat, and to the transmitter 250. In addition, the transistor's output is coupled to its own input so that, once the transistor is turned on, it remains on, even after the second battery 230 dies.

Figure 6:
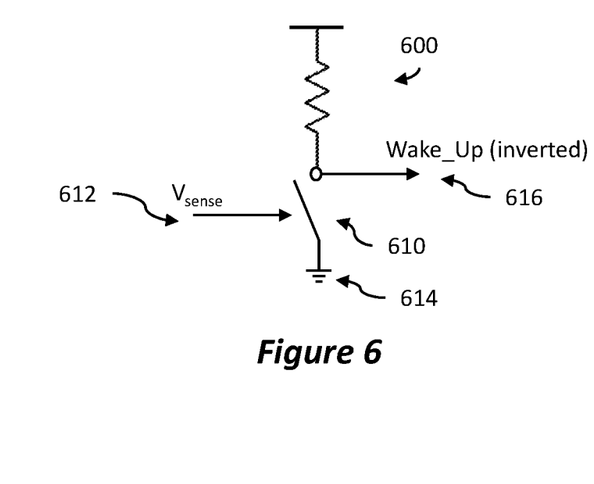

FIG. 6 shows another example wake-up circuit 600 which includes voltage controlled switch 610 that selectively connects a wake-up line 616 to ground 614 based on an input voltage 612 from a wake-up battery. In this example, the wake-up line 616 is inverted such that before the switch 610 is closed, the wake-up line 616 is held high by the second battery, but when the switch 610 closes, the wake-up line 616 is pulled low, thereby activating circuitry on the sensor, such as a processor or RF transmitter. While the switch 610 in this example is shown as a voltage-controlled switch, any suitable switch may be employed.

In some examples, the wake-up circuit may include different types of circuits. For example, the wake-up circuit may include a current threshold detector, a ring oscillator, a power-on-reset circuit, or an NMOS footer switch. In some examples, the activator 420 may include a DC-DC converter, a clock circuit, or a processor. For example, the detector 410 may output a signal to turn on a DC-DC converter that connects a battery to a sensor element. In some examples, the detector 410 may output a signal that is provided as a signal to a processor or to a clock circuit. For example, the processor may power on based on a power-on-reset signal and draw power from the battery 220 and supply a voltage to the sensor element. A clock circuit of the wake-up circuit, such as a ring oscillator, may be used to generate a clock signal for another circuit, such as a processor clock to activate the processor, which begins drawing power from the battery 220. An NMOS footer switch may close to supply power from the battery 220 to a processor or another circuit to activate the sensing element.

Figure 7:
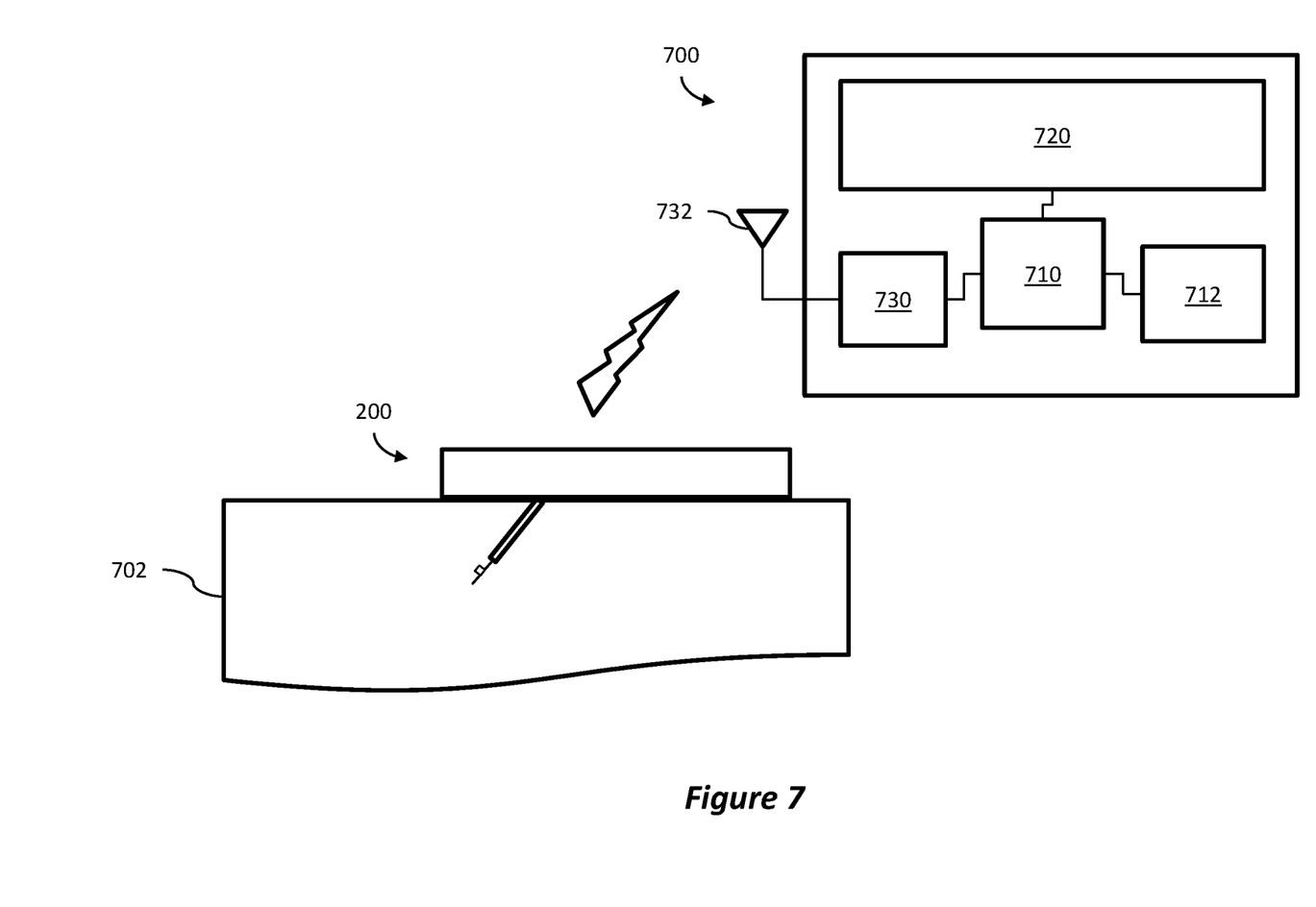
FIG. 7 shows an example system for biosensors with wake-up batteries.

Referring now to FIG. 7, FIG. 7 shows an example system that includes the glucose sensor 200 of FIG. 2, which is attached to a patient and the sensor element 210 has been inserted into the patient's skin, though other suitable biosensors may be used in example systems according to this disclosure, such as those shown in FIGS. 1 and 3. The system also includes a computing device 700 that can receive sensor information from the glucose sensor 200 when it is in range of the sensor's RF transmitter 250.

The computing device 700 includes a processor 710 and a memory 720, which are used by the computing device 700 to execute software for obtaining information from the glucose sensor 700 and store such information in the memory 720. The display 720 can provide a user interface and can provide sensor information that has been obtained from the glucose sensor 200. The computing device 700 also includes a radio transceiver 730 and antenna 732. In this example, the radio transceiver 730 is an RFID transceiver that emits RF signals to the glucose sensor 200, which then transmits sensor information to the computing device. However, other suitable computing devices 700 according to this disclosure may have other types of radio receivers or transceivers, such as an NFC transceiver, a BlueTooth™ transceiver, or a wireless local area network ("WLAN") transceiver, such as a WiFi transceiver. Selection of the appropriate transceiver may depend on the type transmitter 250 within the sensor 200.

Figure 8:
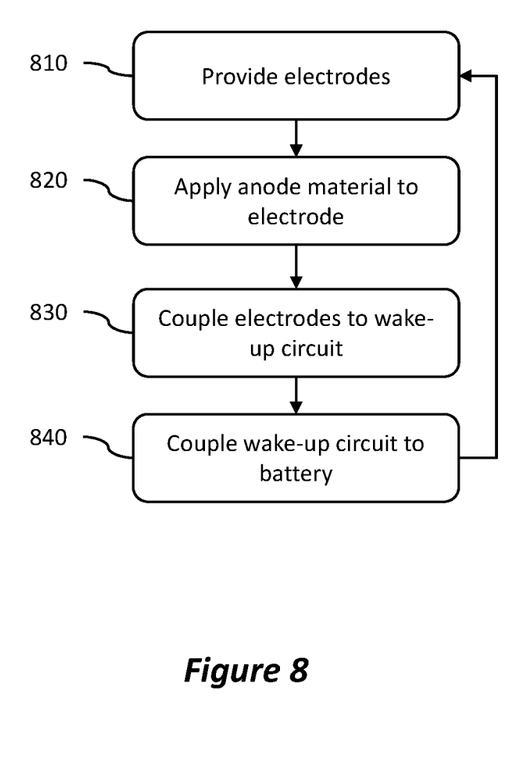
FIG. 8 shows an example method of manufacture of a biosensor with a wake-up battery.

Referring now to FIG. 8, FIG. 8 shows a method of manufacturing a biosensor with a wake-up battery.

At block 810, an electrode and a counter electrode are provided. As discussed above, the electrode may be a platinum or platinum coated wire. The counter electrode may be a Ag/AgCl. In one example, a platinum layer may be applied to base wire by a suitable technique, including electroplating or physical vapor deposition, including evaporation and sputtering techniques. A counter electrode material, such as Ag/AgCl may be deposited or formed over a portion of the electrode. For example, the counter electrode material may be deposited, sintered, overlaid, or otherwise applied to the electrode. In some examples, the counter electrode may be formed separately from the electrode. For example, an Ag/AgCl wire or Ag/AgCl coated wire may be employed as a counter-electrode.

At block 820, an anode material is applied near or at one end of the electrode. In this example, the anode material is zinc; however, other suitable materials may be used, such as iron, aluminum, or nickel. As discussed above, the amount of anode material that is deposited on the electrode can depend on the amount of power needed to "wake-up" the biosensor 200. In some examples, a suitable amount of anode material may be 10-100 ng for a zinc, iron, or nickel anode material, while a suitable amount of aluminum may be 3-30 ng.

At block 830, the electrode and counter electrode are coupled to a potentiostat within the wake-up circuit. Examples of suitable wake-up circuits are discussed above with respect to FIGS. 4-6. In this example, the electrode and counter electrode are coupled to a $V_{sense}$ input of the wake-up circuit.

At block 840, the wake-up circuit is coupled to the battery. In this example, the wake-up circuit is coupled to the battery by a resistor that is selectably-coupled to a voltage-controlled switch. The voltage-controlled switch is initially set to an open position, but that when the wake-up circuit is activated, the wake-up circuit closes the switch to provide a wake-up signal to a processor.

Figure 9:
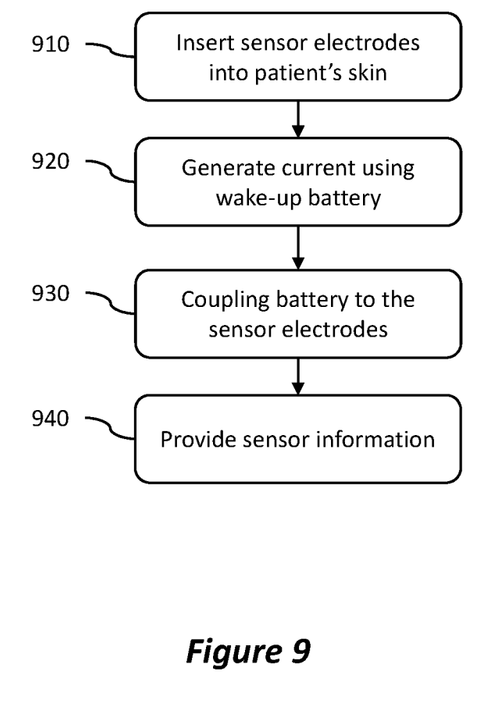
FIG. 9 shows an example method of use of a biosensor with a wake-up battery.

Referring now to FIG. 9, FIG. 9 shows a method of using a biosensor with a wake-up battery. The method of FIG. 9 will be described with respect to the example glucose sensor 200 shown in FIG. 2; however, the method is not limited to such a glucose sensor 200. Rather, the method may be performed with any suitable biosensor with a wake-up battery according to this disclosure.

At block 910, the biosensor's electrode 212 and counter-electrode 214 are inserted into the patient's skin and exposed to the patient's interstitial fluid. In addition, the anode material 232 of the wake-up battery 230 is immersed in the interstitial fluid. The anode material 232 and the counter electrode 214, upon immersion in the patient's interstitial fluid, activate the wake-up battery 230.

At block 920, the wake-up battery generates a voltage and a current which are transmitted to the wake-up circuit 240 after being immersed in the interstitial fluid.

At block 930, the wake-up circuit 240, in response to receiving the voltage and current from the wake-up battery 230, couples the battery 220 to the electrode 212 and the counter electrode 214 via a potentiostat to trigger a GOX/glucose reaction in the patient's interstitial fluid.

At block 940, current generated by the GOX/glucose reaction is sensed and the sensed current level is transmitted by the wireless transmitter 250 and antenna 252. In one example, the wireless transmitter 250 may transmit sensor information irrespective of the presence of a remote device, but in some examples, the wireless transmitter 250 may transmit sensor information in response to the presence of an RFID or NFC signal.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Some example biosensors with wake-up batteries according to this disclosure may include a processor. The biosensor may include a computer-readable medium, such as a random access memory (RAM) coupled to the processor. The processor can execute computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable storage media, that may store instructions that, when executed by the processor, can cause the processor to perform the steps described herein as carried out, or assisted, by a processor. Examples of computer-readable media may include, but are not limited to a memory chip, ROM, RAM, ASIC, or any other medium from which a computer processor can read or write information. The processor, and the processing, described may be in one or more structures, and may be dispersed through one or more structures. The processor may comprise code for carrying out one or more of the methods (or parts of methods) described herein.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

That which is claimed is:

1. A device comprising:
   a first electrode having a distal end for insertion into a subcutaneous layer beneath a patient's skin, and
   a second electrode coupled to the first electrode, a distal portion of the second electrode for insertion into the subcutaneous layer,
   an anode material physically coupled to a portion of the distal end of the first electrode, the anode material for insertion into the subcutaneous layer,
   wherein the first and second electrodes form a portion of a biosensor, and wherein the anode material and the second electrode form a portion of a first battery, wherein the first battery activates and generates an electrical signal in response to immersion in an electrolytic fluid, and wherein the anode material depletes over time while the first battery is active;
   a second battery comprising two terminals to apply a voltage across the first and second electrodes, at least one of the two terminals electrically decoupled from the first and second electrodes; and
   a wake-up circuit coupled to the first battery to receive the electrical signal from the first battery and, in response, to electrically couple the second battery to the first and second electrodes.

2. The device of claim 1, further comprising a glucose oxidase material disposed on a portion of the distal end of the first electrode.

3. The device of claim 1, further comprising a radio frequency ("RF") transmitter, and wherein:
   the second battery is at least partially electrically decoupled from the RF transmitter and is further to apply power to the RF transmitter, and
   the wake-up circuit is further to electrically couple the second battery to the RF transmitter in response to receiving the signal from the first battery.

4. The device of claim 1, wherein:
   the first electrode comprises a platinum material;
   the second electrode comprises a silver/silver-chloride material coating a portion of the first electrode; and
   the anode material comprises zinc, iron, aluminum, or nickel.

5. The device of claim 1, wherein the anode material comprises approximately 10 to 100 nanograms ("ng") of zinc, approximately 10 to 100 ng of nickel, approximately 10 to 100 ng of iron, or approximately 3 to 30 ng of aluminum.

6. The device of claim 1, wherein the wake-up circuit comprises one or more of (1) a voltage threshold detection circuit and a reference voltage source, (2) a current threshold detection circuit and a reference current source, (3) a ring oscillator, (4) a power-on reset circuit, or (5) an NMOS footer switch.

7. The device of claim 1, wherein the device further comprises a processor, and wherein the wake-up circuit is further to electrically couple the second battery to the processor.

8. The device of claim 7, wherein the wake-up circuit comprises a ring oscillator electrically coupled to a clock circuit of the processor to activate the clock circuit after receiving the signal from the first battery.

9. The device of claim 1, wherein the first battery is configured to output a predetermined voltage or current for a predetermined period of time based on an amount of anode material.

10. A method comprising:
    providing first and second electrodes, the first electrode having a distal end for insertion into a subcutaneous layer beneath a patient's skin, the second electrode coupled to the first electrode, a portion of the second electrode for insertion into the subcutaneous layer;
    applying an anode material to a portion of the distal end of the first electrode;
    coupling a wake-up circuit to the first and second electrodes to receive an electrical signal from a first battery in response to immersion of the first battery in an electrolytic fluid, the anode material and the portion of the second electrode forming a portion of a first battery, wherein the anode material is configured to deplete over time while the first battery is active; and
    coupling a second battery to the wake-up circuit, the wake-up circuit to electrically couple the second battery to the first and second electrodes in response to the signal from the first battery.

11. The method of claim 10, further comprising a glucose oxidase material disposed on a portion of the distal end of the first electrode.

12. The method of claim 10, further comprising coupling a radio frequency ("RF") transmitter to the wake-up circuit, and wherein:
    the second battery is at least partially electrically decoupled from the RF transmitter and is further to apply power to the RF transmitter, and
    the wake-up circuit is further to electrically couple the second battery to the RF transmitter in response to receiving the signal from the first battery.

13. The method of claim 10, wherein:
    the first electrode comprises a platinum material;
    the second electrode comprises a silver/silver-chloride material coating a portion of the first electrode; and
    the anode material comprises zinc, iron, aluminum, or nickel.

14. The method of claim 10, wherein the anode material comprises approximately 10 to 100 nanograms ("ng") of zinc, approximately 10 to 100 ng of nickel, approximately 10 to 100 ng of iron, or approximately 3 to 30 ng of aluminum.

15. A method comprising:
    inserting a distal end of a first electrode and a portion of a second electrode into a patient's skin and into the patient's interstitial fluid, the first and second electrodes forming a portion of a biosensor of a device, the first electrode coupled to the second electrode, wherein an anode material is coupled to a portion of a distal end of the first electrode, the anode material and the second electrode forming a portion of a first battery;

the device further comprising a second battery comprising two terminals to apply a voltage across the first and second electrodes, at least one of the two terminals electrically decoupled from the first and second electrodes, generating an electrical signal by the first battery in response to the anode material and the portion of the second electrode being immersed in the patient's interstitial fluid, wherein the anode material depletes over time while the first battery is active; and electrically coupling the second battery to the first and second electrodes by a wake-up circuit of a device in response to receiving the electrical signal from the first battery, the device comprising the biosensor.

16. The method of claim 15, further comprising obtaining sensor information from the biosensor and transmitting the sensor information to a remote wireless device.

17. The method of claim 16, wherein the transmitting is performed using a radio frequency identification ("RFID") or near-field communication ("NFC") technique.

18. The method of claim 15, wherein the device comprises a processor, and further comprising activating a clock circuit of the processor by the wake-up circuit.

19. The method of claim 15, further comprising providing sensor information from the biosensor to a radio frequency ("RF") transmitter.

* * * * *